US 8,542,876 B1

(12) United States Patent
Engel et al.

(10) Patent No.: US 8,542,876 B1
(45) Date of Patent: Sep. 24, 2013

(54) METHODS AND SYSTEMS FOR ENHANCING BACKSCATTER X-RAY FOREIGN OBJECT DEBRIS DETECTION

(75) Inventors: James E. Engel, Newport Beach, CA (US); Rodney Stephen Wright, Huntington Beach, CA (US); Chin Hoi Toh, Orange, CA (US); William Talion Edwards, Foristell, MO (US)

(73) Assignee: The Boeing Company, Chicago, IL (US)

( * ) Notice: Subject to any disclaimer, the term of this patent is extended or adjusted under 35 U.S.C. 154(b) by 255 days.

(21) Appl. No.: 13/073,084

(22) Filed: Mar. 28, 2011

(51) Int. Cl.
*G06K 9/00* (2006.01)
(52) U.S. Cl.
USPC .............................. 382/103; 382/275; 378/87
(58) Field of Classification Search
USPC ................. 382/100, 103, 106–108, 132, 141, 382/143, 149, 152–153, 168, 181, 199, 209, 382/219, 232, 254, 276, 287–291, 505, 312–321, 382/275; 378/87, 58, 57
See application file for complete search history.

(56) References Cited

U.S. PATENT DOCUMENTS

| | | | |
|---|---|---|---|
| 5,299,253 A | 3/1994 | Wessels | |
| 5,600,303 A | 2/1997 | Husseiny et al. | |
| 5,642,394 A | 6/1997 | Rothschild | |
| 5,763,886 A | 6/1998 | Schulte | |
| 6,094,472 A | 7/2000 | Smith | |
| 6,466,643 B1 | 10/2002 | Bueno et al. | |
| 6,507,635 B2 | 1/2003 | Birdwell et al. | |
| 6,614,872 B2 | 9/2003 | Bueno et al. | |
| 6,618,465 B2 | 9/2003 | Mohr et al. | |
| 6,636,581 B2 | 10/2003 | Sorenson | |
| 6,665,373 B1 | 12/2003 | Kotowski et al. | |
| 6,873,344 B2 | 3/2005 | Samra et al. | |
| 6,895,073 B2 | 5/2005 | Shih et al. | |
| 7,209,539 B2 * | 4/2007 | De Smet | 378/57 |
| 7,266,174 B2 * | 9/2007 | Birdwell et al. | 378/58 |
| 7,463,714 B2 * | 12/2008 | Edwards et al. | 378/87 |
| 7,508,910 B2 | 3/2009 | Safai et al. | |
| 7,623,626 B2 * | 11/2009 | Safai et al. | 378/87 |

\* cited by examiner

*Primary Examiner* — Seyed Azarian
(74) *Attorney, Agent, or Firm* — Armstrong Teasdale LLP

(57) ABSTRACT

A method for detecting an anomaly associated with a structure is described. The method includes obtaining a baseline scan of the structure, changing at least one condition associated with the structure which is intended to impart a movement of the structure or a movement of objects within the structure, obtaining a secondary scan of the structure, the secondary scan obtained from a same position, with respect to the structure, as the baseline scan, determining any differences between the baseline scan and the secondary scan, and identifying at least one of a foreign object proximate the structure and a structural anomaly associated with the structure based on any differences between the baseline scan and the secondary scan.

20 Claims, 11 Drawing Sheets

METHODS AND SYSTEMS FOR ENHANCING BACKSCATTER X-RAY FOREIGN OBJECT DEBRIS DETECTION

BACKGROUND

The field of the disclosure relates generally to foreign object debris (FOD) detection, and more specifically, to methods and systems for enhancing backscatter x-ray FOD detection.

As is known, aircraft and other complex structures are fabricated and subsequently modified in manners that sometimes require substantial disassembly and re-assembly of portions thereof. During fabrication, for example, it is common to place components together for a drilling operation and then separate such components for deburring operations prior to a final assembly of such components. Such operations result in FOD from the metal or composite shavings that result from the drilling and deburring operations. The tools and bits tools used to accomplish such operations, if left in a position and forgotten, may also end up as FOD. Likewise, the drilling plates used to properly align the drilling tools and bits can end up as FOD if not properly disposed of. In fact, FOD could be any type of objects unintentionally left in a fabricated structure.

In the aircraft example, modifications may involve the removal of exterior and/or interior panels to facilitate access to components of the aircraft that are contained within compartments located behind the panels. When such panels are removed, foreign objects are often introduced into the compartments. Items such as tools, fasteners, manufacturing material, personal objects, and other debris may be inadvertently left behind in such compartments after the modifications are complete. Such items constitute FOD.

Thus, is it easy to understand that during fabrication and modification of aircraft, as well as other complex assemblies such as land vehicles, water vehicles, electrical boxes and other complex machinery, there are opportunities to unintentionally leave items and other debris behind in the areas where work was performed.

As is easily understood, the presence of FOD in an aircraft or other complex machine is undesirable as the FOD may interfere with proper operation of such machines. However, once the fabrication and/or modifications have been completed to such machines, it is difficult to determine whether or not there is FOD present. One contemporary practice is to have technicians visually inspect work areas. However, such visual inspection is too often insufficient as FOD may be overlooked because of accessibility and inefficiency of manual inspection tools.

In addition, processes are known in which images taken using backscatter X-ray imaging technology are subtracted from one another, but these processes do not enhance the detection of hidden FOD. Specifically, existing X-ray processes image everything within the structure and are difficult to interpret because the multiple layers and hardware associated with such structures can mask FOD that may be hidden and not clearly visible in the image.

BRIEF DESCRIPTION

In one aspect, a method for detecting an anomaly associated with a structure is provided. The method includes obtaining a baseline scan of the structure, changing at least one condition associated with the structure which is intended to impart a movement of the structure or a movement of objects within the structure, obtaining a secondary scan of the structure, the secondary scan obtained from a same position, with respect to the structure, as the baseline scan, determining any differences between the baseline scan and the secondary scan, and identifying at least one of a foreign object proximate the structure and a structural anomaly associated with the structure based on any differences between the baseline scan and the secondary scan.

In another aspect, a method for determining whether any foreign object debris is associated with a structure is provided. The method includes obtaining a baseline scan of the structure, causing a movement of the structure significant enough to cause a movement of any foreign object debris that is associated with the structure, obtaining a secondary scan of the structure, the secondary scan obtained from a same position, with respect to the structure, as the baseline scan, determining any differences between the baseline scan and the secondary scan, and identifying any foreign object debris associated with the structure based on the determined differences.

In still another aspect, a method for detecting foreign object debris and structural anomalies associated with an aircraft is provided. The method includes interrogating a portion of an aircraft with an X-ray source, applying a physical load to the aircraft, subsequently interrogating substantially a same portion of the aircraft with the X-ray source after the application of the physical load, comparing images resulting from the X-ray interrogations to determine any differences, and identifying the objects or displacements, that resulted in the differences as one of potential foreign object debris and a structural anomaly.

The features, functions, and advantages that have been discussed can be achieved independently in various embodiments or may be combined in yet other embodiments further details of which can be seen with reference to the following description and drawings.

DETAILED DESCRIPTION

The described embodiments are directed to processes and systems for detection of foreign object debris (FOD) inside a structure by moving any entrapped FOD in between the acquisition of backscatter X-ray images. The two images are subjected to an image subtraction process to remove the overlying structure leaving a difference image based on a shifting position of any FOD. As such, a method is provided that substantially improves the probability of detecting FOD using backscatter X-ray images as only FOD remains in the subtracted image.

Figure 1:
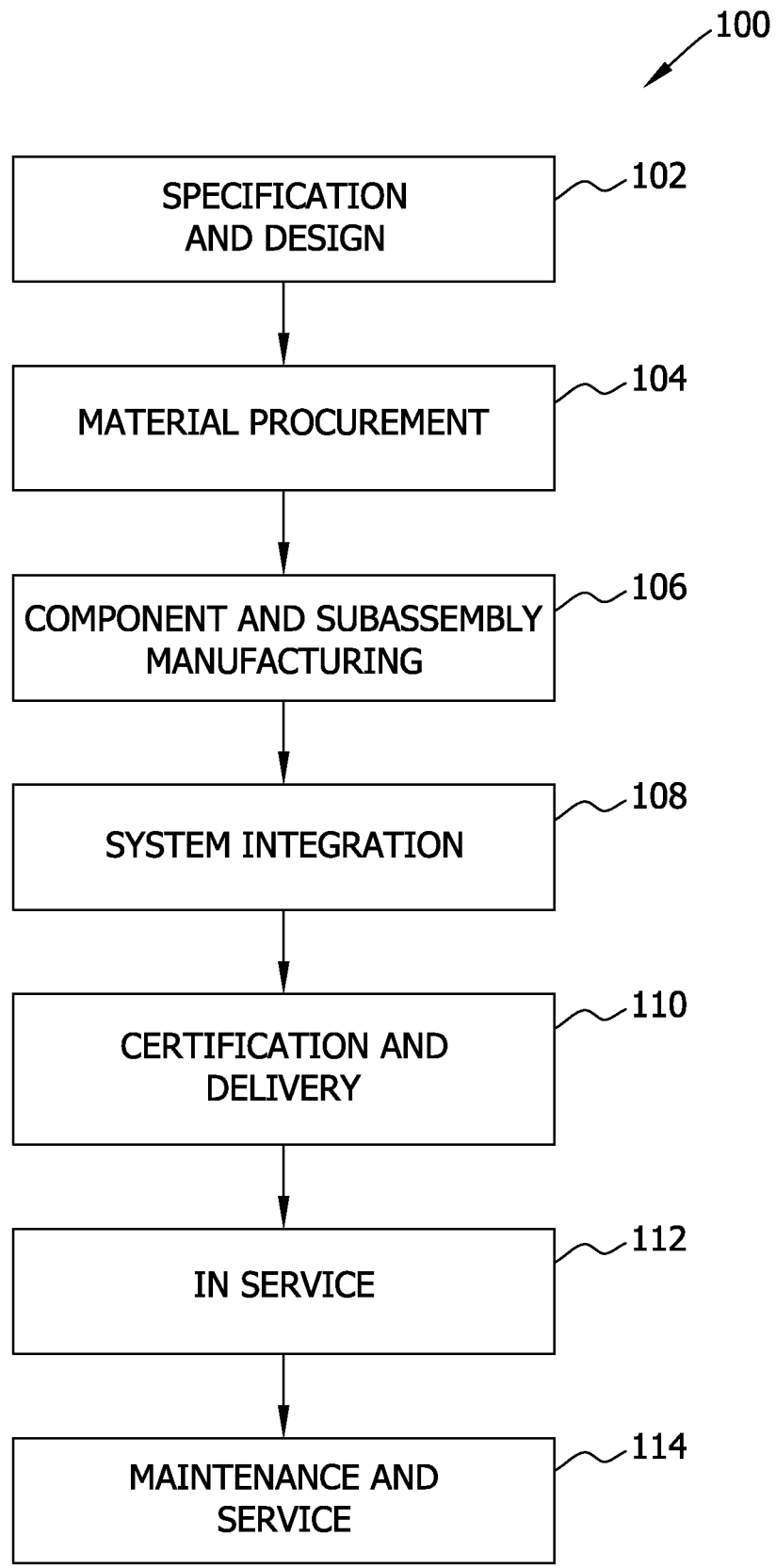
FIG. 1 is a flow diagram of an aircraft production and service methodology.
Figure 2:
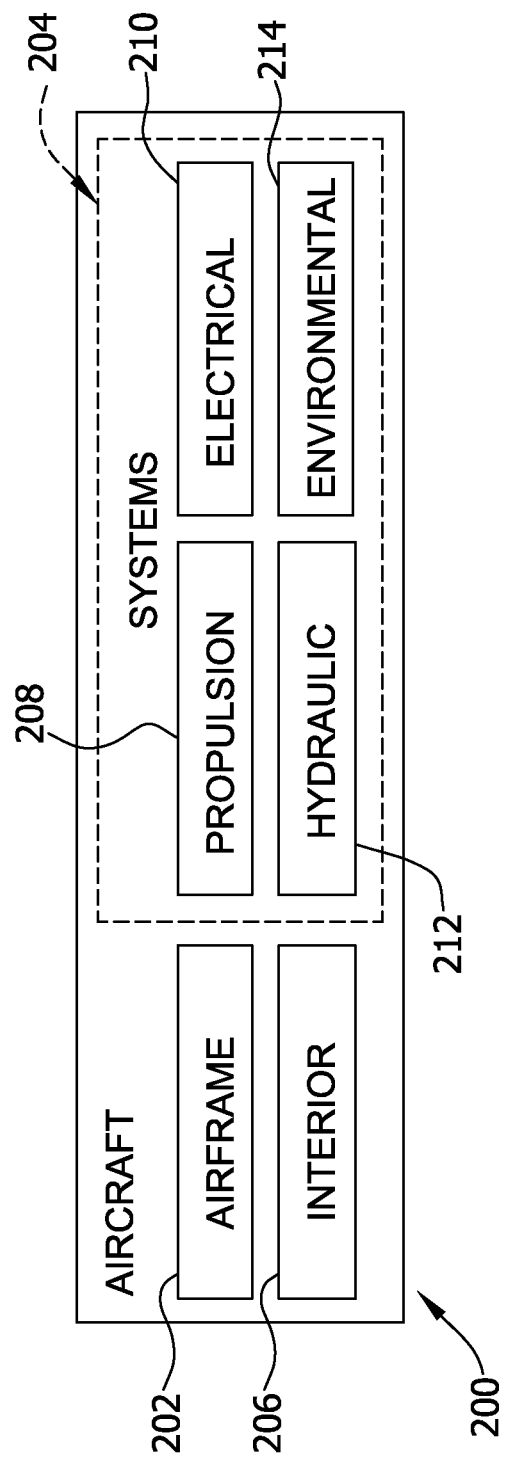
FIG. 2 is a block diagram of an aircraft.

Referring more particularly to the drawings, embodiments of the disclosure may be described in the context of aircraft manufacturing and service method 100 as shown in FIG. 1 and an aircraft 200 as shown in FIG. 2. During pre-production, aircraft manufacturing and service method 100 may include specification and design 102 of aircraft 200 and material procurement 104.

During production, component and subassembly manufacturing 106 and system integration 108 of aircraft 200 takes place. Thereafter, aircraft 200 may go through certification and delivery 110 in order to be placed in service 112. While in service by a customer, aircraft 200 is scheduled for routine maintenance and service 114 (which may also include modification, reconfiguration, refurbishment, and so on).

Each of the processes of aircraft manufacturing and service method 100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 2, aircraft 200 produced by aircraft manufacturing and service method 100 may include airframe 202 with a plurality of systems 204 and interior 206. Examples of systems 204 include one or more of propulsion system 208, electrical system 210, hydraulic system 212, and environmental system 214. Any number of other systems may be included in this example. Although an aerospace example is shown, the principles of the disclosure may be applied to other industries, such as the automotive, petro-chemical, ship building or construction industries.

Apparatus and methods embodied herein may be employed during any one or more of the stages of aircraft manufacturing and service method 100. For example, without limitation, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during component and subassembly manufacturing 106 and system integration 108, for example, without limitation, by substantially expediting assembly of or reducing the cost of aircraft 200. Similarly, one or more of apparatus embodiments, method embodiments, or a combination thereof may be utilized while aircraft 200 is in service, for example, without limitation, to maintenance and service 114 may be used during system integration 108 and/or maintenance and service 114 to determine whether parts may be connected and/or mated to each other.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Figure 3:
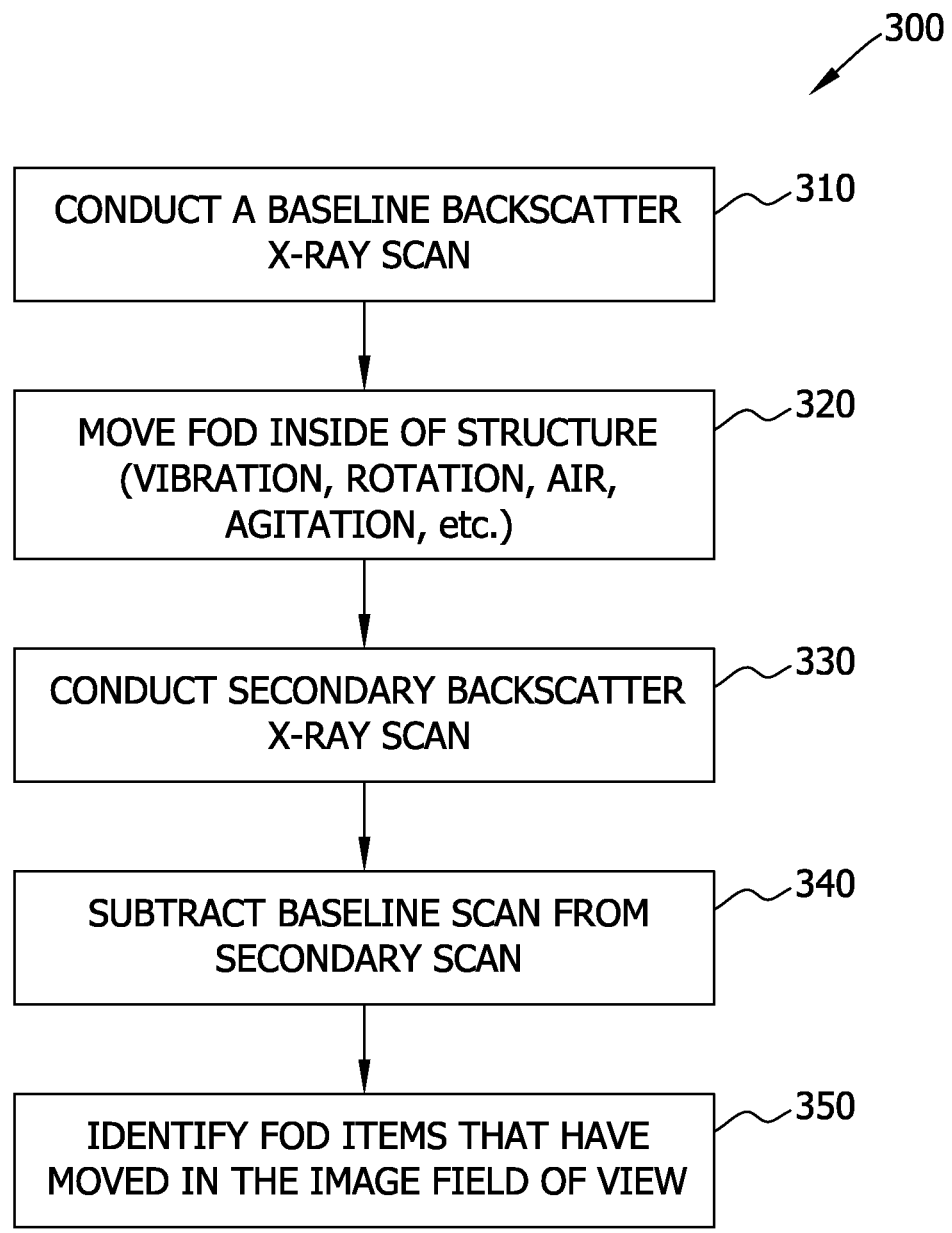
FIG. 3 is a flowchart illustrating a foreign object debris (FOD) detection process.

Turning now to FIG. 3, a flowchart 300 illustrating one embodiment of a FOD detection process is provided. Flowchart 300 illustrates a method to make foreign object debris (FOD) readily detectable using backscatter X-ray image. A first backscatter X-ray image is subtracted from a second backscatter X-ray image which removes the overlying structure from the resulting difference image. By imparting a movement on the structure, and therefore any FOD therein, between the acquisitions of the two images, only the difference caused by the movement of the FOD remains in the difference image.

Since the structure is removed from the difference image, only the FOD that has been moved remains in the difference image. Since the FOD has been moved, the FOD can easily be identified. As described above, existing backscatter X-ray image solutions require time-consuming interpretation and as a result users are often unable to detect any FOD remaining within the structure. As shown in FIG. 3, the overlying structure within the images that makes interpretation of such X-ray images difficult is removed.

Referring specifically to flowchart 300, a baseline (first) image of the structure is obtained 310 using, for example, backscatter X-ray imaging equipment. In embodiments, the baseline image is digitally stored. The FOD is then moved 320 within the structure. One example of a mechanism to displace (move) any existing FOD includes rotating the structure in an attempt to move any FOD therein and then returning the structure to its original position. The force of gravity will generally cause any FOD within the structure being rotated to change position. Another example includes utilizing compressed air and/or pneumatics to try to move any FOD within the structure, such as, blowing forced air through or across or within the structure. Still another example is the utilization of an external device to vibrate or agitate or rotate the structure to attempt to reposition any FOD therein. These and other methods are intended to move 320 the hidden FOD within such structures.

Once the structure is returned to its original position, a secondary (second) backscatter X-ray image is obtained 330 with the area of interest of the structure in the same position as when the baseline image was obtained 310. The secondary image is also digitally stored. While described as being in the original position when the secondary image is obtained, it is merely necessary that the position of the structure is in the same position with respect to the backscatter X-ray imaging device when the two images are obtained 310, 330. For example, one method used to ensure the position of the structure is in the same position with respect to the backscatter X-ray imaging device during the acquisition of the two images is to use fiduciary position markers on the structure.

The original digitally stored image (the baseline image) is subtracted 340 from the secondary digitally stored image using one or more image processing software applications to reveal the differences between the images. In certain applications, the second image may be subtracted from the first image. In an embodiment, the differences are stored as what is referred to herein as a difference image. The difference image is interpreted to identify 350 articles (i.e., FOD) that have changed position. For example, the original position of a particular foreign object and a new position for the foreign object can be determined based upon the negative or positive shading within the difference image(s) created by the subtraction process.

With regard to FOD detection, the process illustrated by FIG. 3 provides a capability to find hidden FOD including manufacturing debris, lost tools, bits, misplaced components and/or hardware such as nuts, washers and bolts, as well as metallic and non-metallic materials that could potentially be inadvertently misplaced during fabrication or modification of an aircraft or other complex structure.

Figure 4:
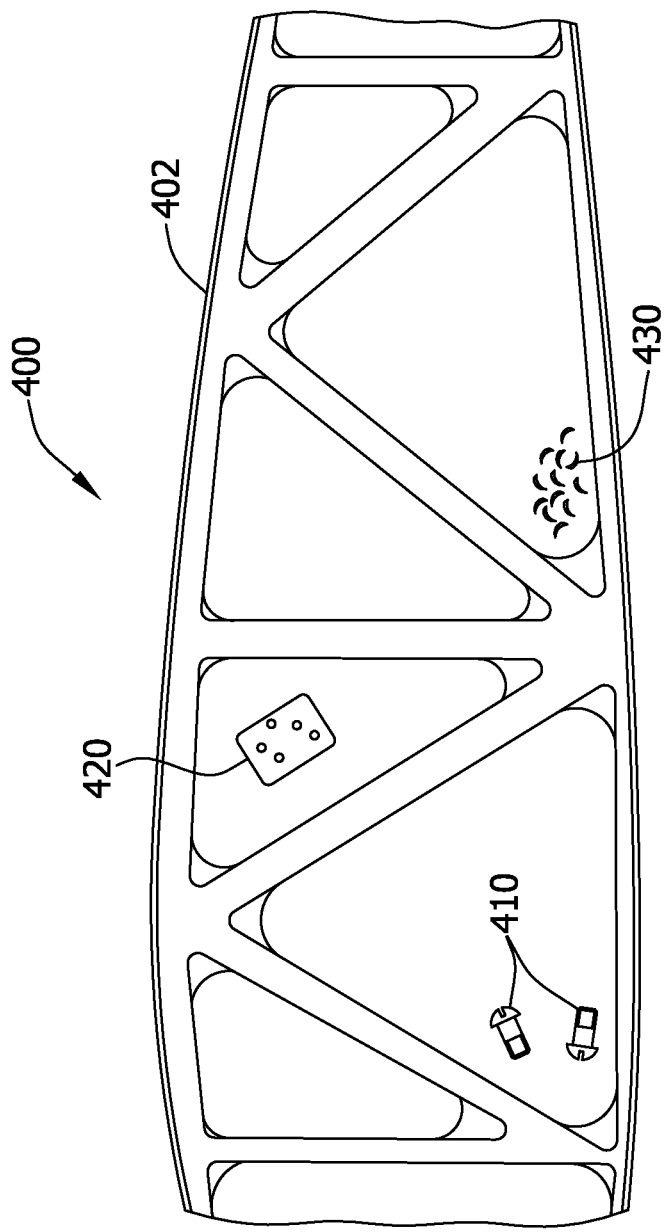
FIG. 4 depicts a baseline X-ray image of a portion of an aircraft with potential FOD items therein.

FIG. 4 is a representation of an image 400 of a portion 402 of an aircraft. For correlation with the method illustrated by FIG. 3, image 400 may be considered a baseline image. As shown in image 400, the X-ray has indicated potential FOD, including rivets 410, drill plate 420, and shavings 430. Image 400 is an exaggeration for purposes of illustration as in the typical case; such FOD is not so easily identifiable.

Figure 5:
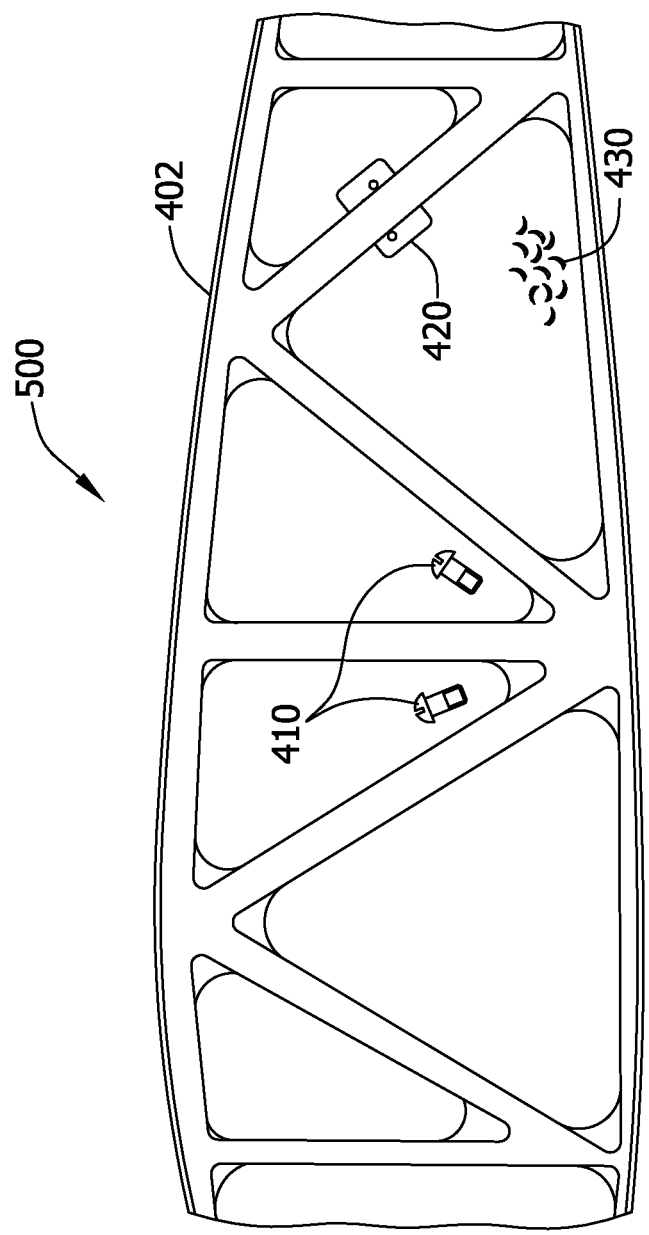
FIG. 5 depicts a second X-ray image of the same portion of the aircraft, the second X-ray image corresponding to the baseline image of FIG. 4 after agitation of any FOD therein.

After the aircraft portion 402 is moved and/or forces are applied to the aircraft portion as described herein, a second image 500 is obtained, as shown in FIG. 5. Image 500 may be considered a second X-ray image of the portion 402 of the aircraft, and as described herein, the second X-ray image corresponds to the baseline image of FIG. 4. As can be seen in this image depiction, rivets 410, drill plate 420, and shavings 430 have shifted in position due to one or both of a movement of the aircraft portion 402 and a force (compressed air, etc.) being applied to the aircraft portion.

Figure 6:
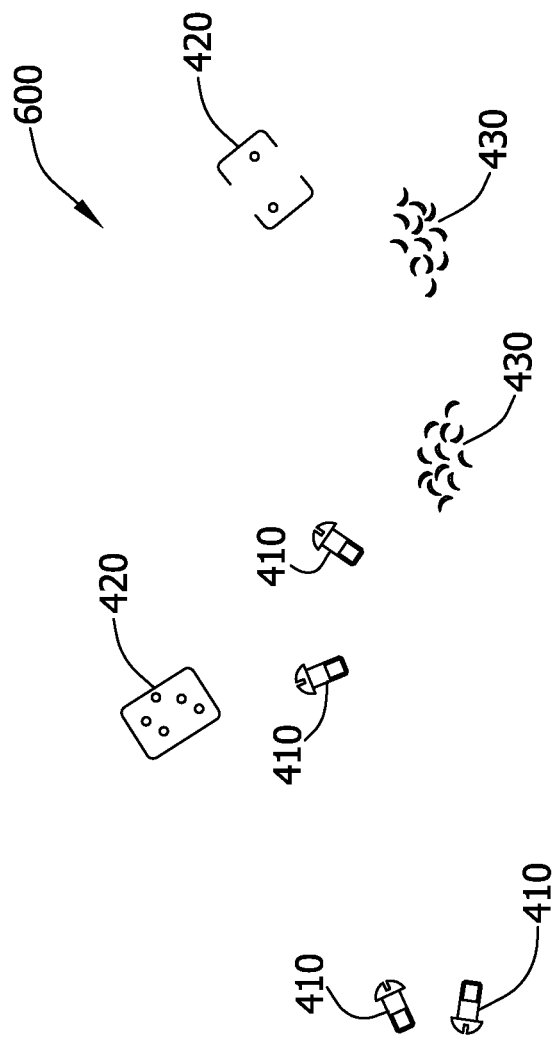
FIG. 6 is a difference image depicting differences between the images of FIGS. 4 and 5, which includes FOD that has shifted position between the time the baseline image was acquired and the time the second image was acquired.

FIG. 6 is a difference image 600 depicting differences between image 400 and image 500 of FIGS. 4 and 5. As easily seen from the exaggeration of FIGS. 4-6, image 600 includes the various FOD (rivets 410, drill plate 420, and shavings 430) that has shifted position between the time the baseline image 400 was acquired and the time the second image 500 was acquired. Notably, since the FOD has shifted position, each instance of FOD will appear twice in the difference image.

Similar to detection of FOD in a broader sense, the described embodiments are also useful in detection of structural anomalies and any other defects within such structures. A typical example would be treating the structural crack or deformation as a form of foreign object debris created after the introduction of physical stresses or forces. In some applications, if a structure, for example a tank assembly, is stressed, the underlying structure may move if there is an anomaly within either the tank or the underlying structure. By positioning a backscatter X-ray system at the correct orientation before and after (or during) the application of the stress, the internal movement within the structure can be assessed utilizing subsequent backscatter X-ray difference images. Methods such as vacuum application, pressurization, and loading are used to apply the stress. While systems are known that measure external surface displacement, the described embodiments are operable to visualize any internal displacements caused by the application of the stress by providing an inside view of the structure.

Figure 7:
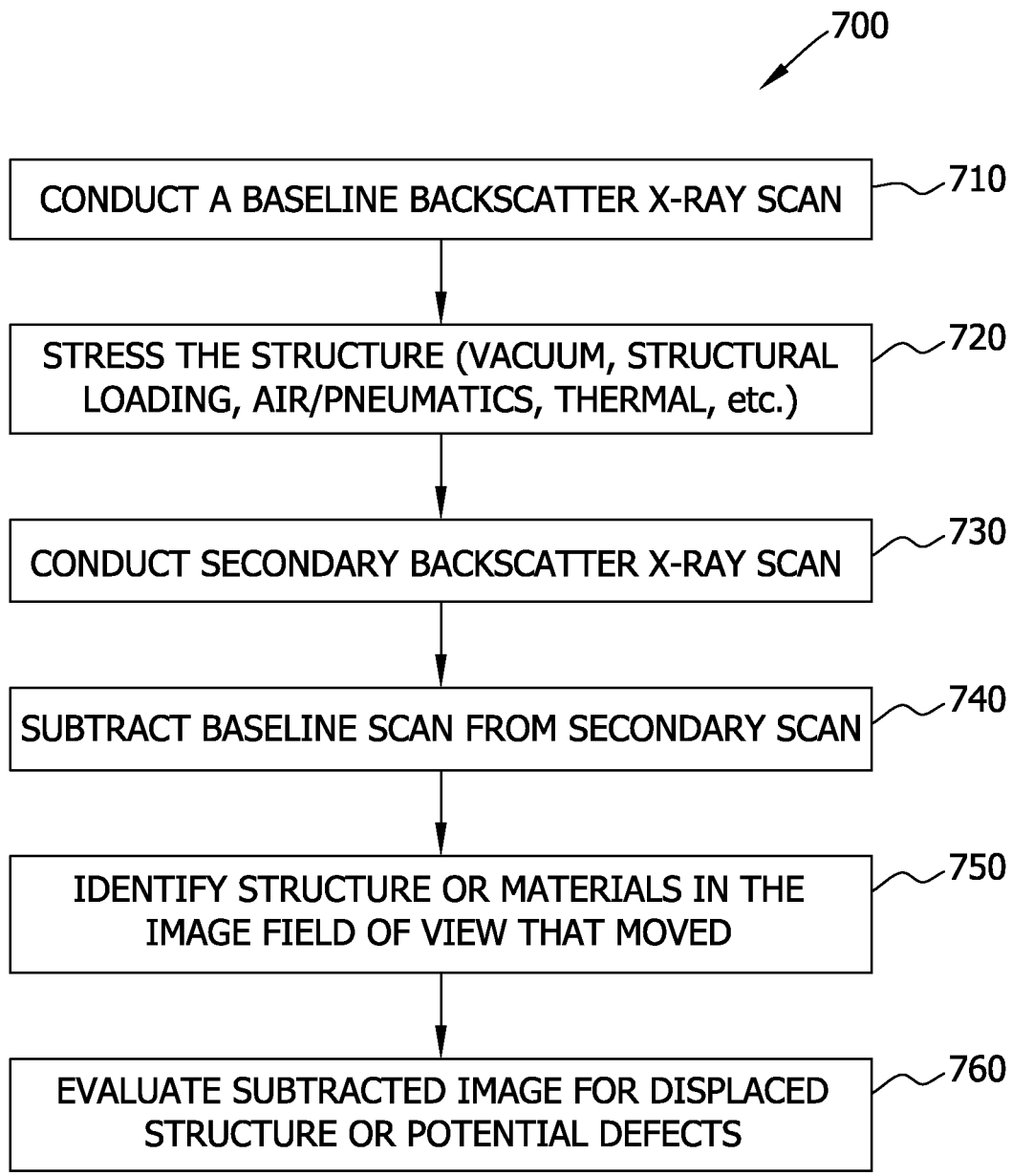
FIG. 7 is a flowchart, similar to the flowchart of FIG. 3, and illustrating structural anomaly detection.

Structural anomaly detection is further illustrated by flowchart 700 of FIG. 7. A baseline (first) image of the structure is obtained 710 using, for example, backscatter X-ray imaging equipment. In embodiments, the baseline image is digitally stored. The structure is then stressed 720 using some form of loading such as application of a vacuum, air/pneumatics pressurization, application of structural loading, and/or application of heating/thermal loading. An alternative to stressing the structure is using time-based images such as monitoring corrosion over time on subsequent backscatter X-ray images.

A secondary (second) backscatter X-ray image is obtained 730 with the area of interest of the structure in the same position as when the baseline image was obtained 710 and either with the load applied or after loading and digitally storing that image. The secondary image is also digitally stored. While described as being in the original position when the secondary image is obtained, it is merely necessary that the position of the structure is in the same position with respect to the backscatter X-ray imaging device when the two images are obtained 710, 730. For example, one method used to ensure the position of the structure is in the same position with respect to the backscatter X-ray imaging device during the acquisition of the two images is to use fiduciary position markers on the structure.

The original digitally stored image (the baseline image) is subtracted 740 from the secondary digitally stored image using one or more image processing software applications to reveal the differences between the images. In certain applications, the second image may be subtracted from the first image. In an embodiment, the differences are stored as what is referred to herein as a difference image. The difference image is interpreted to identify 750 structure or materials in the image field of view that have moved position. The resultant subtracted image is then evaluated 760 for to identify structural anomalies or potential defects that were displaced due to the loading.

Figure 8:
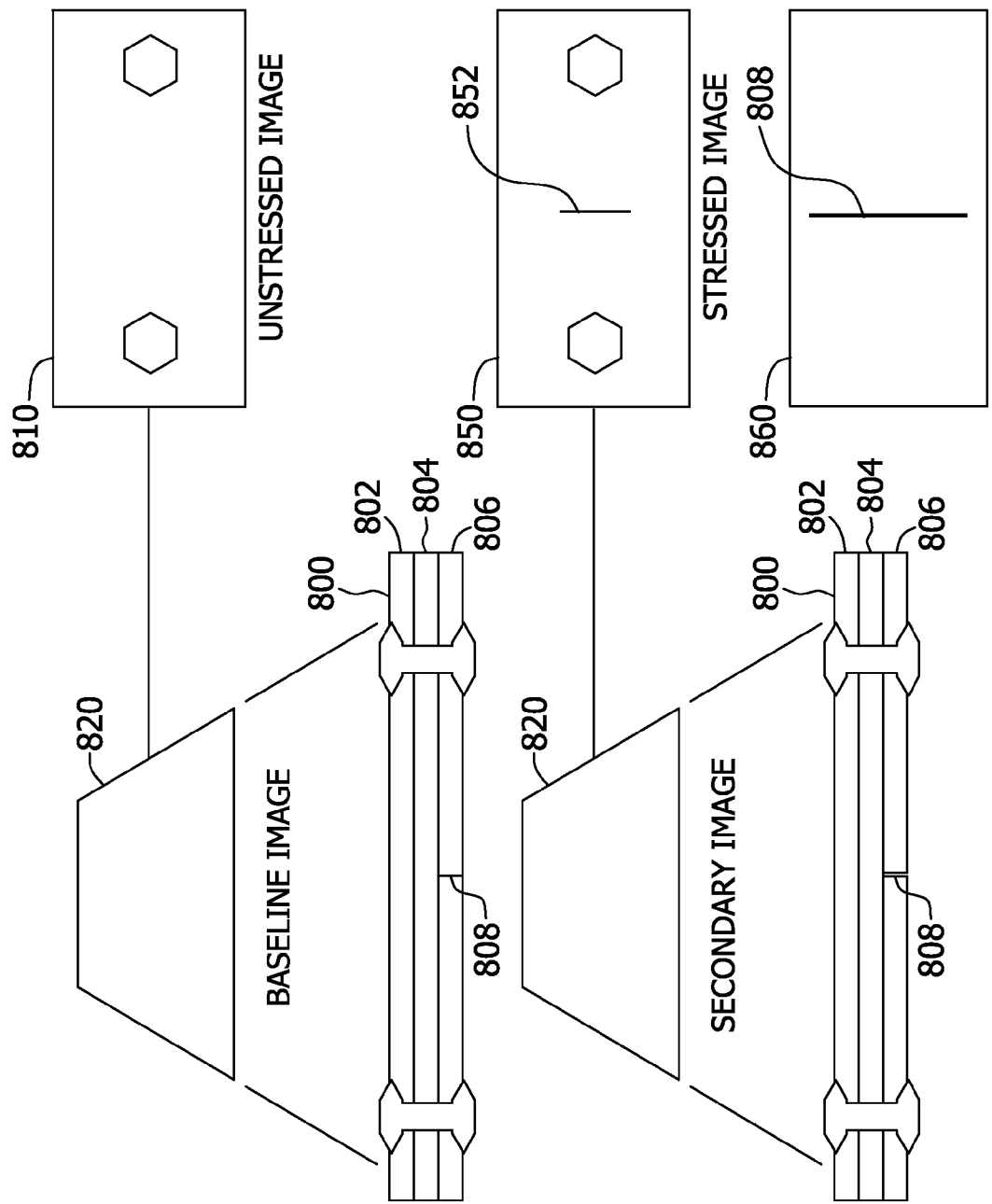
FIG. 8 further illustrates the process of FIG. 7 through an internal crack in a riveted structure example.

FIG. 8 further illustrates the process of FIG. 7 through an internal crack in a riveted structure example. Riveted structure 800 includes three layers 802, 804, and 806, though only layer 802 is visible. A closed crack 808 is in layer 806, though crack 808 is not readily found, due to layer 806 being non-accessible. A baseline image 810 is obtained with an X-ray unit 820 with structure 800 in the unstressed state.

A stress is applied to structure 800, and a secondary image 850 is obtained, in which an image item 852 associated with crack 808 is plainly visible. Subtraction of image 810 and 850 results in a subtracted image 860 where the background of structure 800 is removed and illustrating an image item 862 that is associated with crack 808 and caused by displacement of the structure 800.

Figure 9:
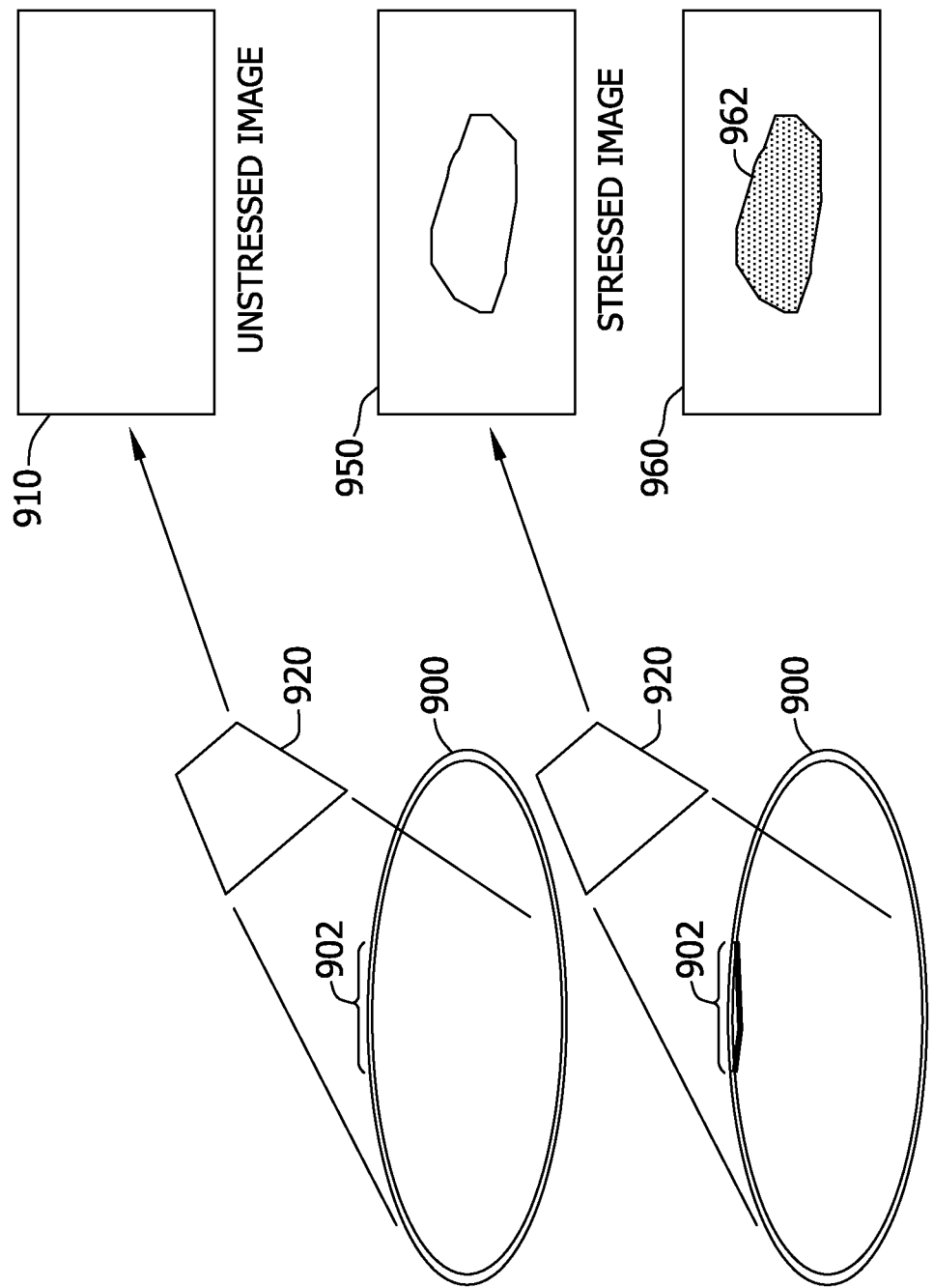
FIG. 9 further illustrates the process of FIG. 7 through an unbond condition in a fuel bladder example.

FIG. 9 further illustrates the process of FIG. 7 through an unbond condition in a fuel bladder example. In a static condition, fuel bladder 900 includes an unbonded portion 902 that is not visible, due to the portion being non-accessible. A baseline image 910 is obtained with an X-ray unit 920 with fuel bladder 900 in the unstressed state.

A stress, for example, in the form of a vacuum, is applied to structure 900, and a secondary image 950 is obtained, in which an image item 952 associated with unbonded portion 902 is plainly visible. Subtraction of image 910 and 950 results in a subtracted image 960 where the background of fuel bladder 900 is removed and illustrating an image item 962 that is associated with unbonded portion 902 and caused by displacement of the fuel bladder 900 by application of the vacuum.

Figure 10:
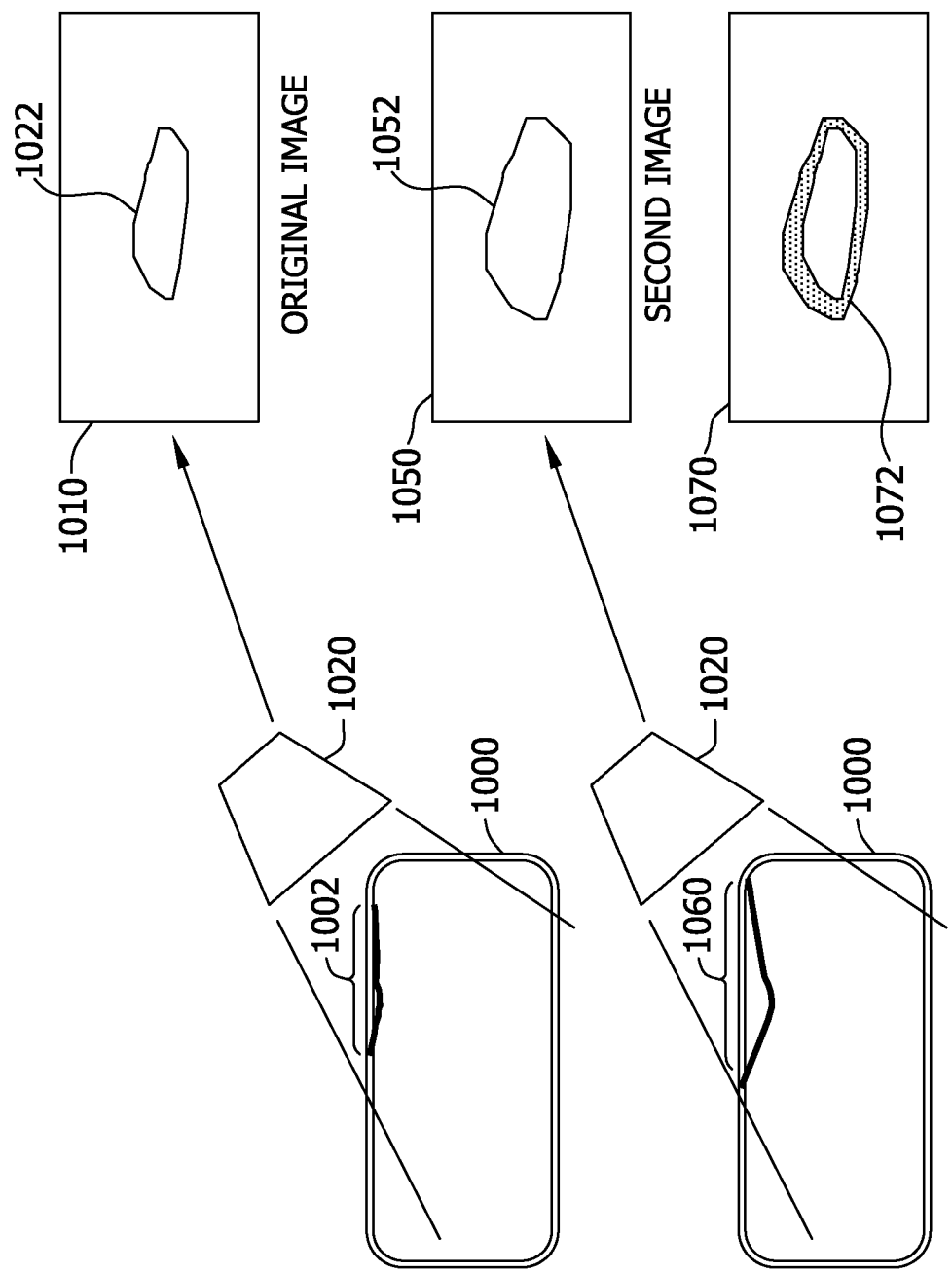
FIG. 10 further illustrates the process of FIG. 7 through a corrosion over time condition that is associated with a wing box.

FIG. 10 further illustrates the process of FIG. 7 through a corrosion over time condition that is associated with a wing box 1000. In a static condition, wing box 1000 includes a small corroded area 1002. A baseline image 1010 is obtained with an X-ray unit 1020 in which an image item 1022 associated with small corroded area 1002 is plainly visible, though not considered to be an issue with operation of wing box 1000. An amount of time passes, and a secondary image 1050 is obtained, in which an image item 1052 associated with an enlarged corroded area 1060 is plainly visible. Subtraction of image 1010 and 1050 results in a subtracted image 1070 where the background of wing box 1000 is removed and illustrating an image item 1072 that is associated with a growth in the corroded area of wing box 1000 caused by passage of time.

Figure 11:
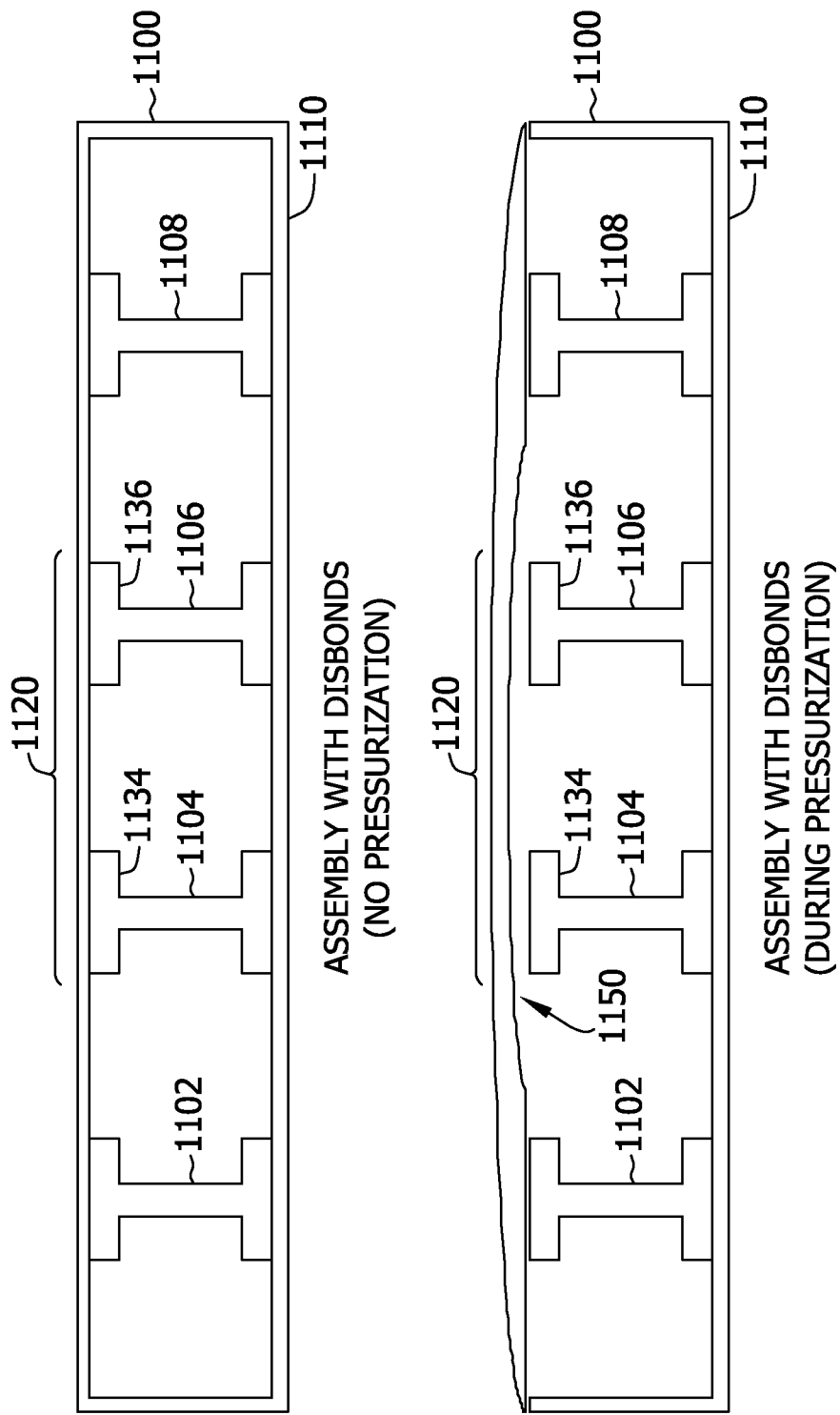
FIG. 11 illustrates structural displacement after pressurization that is visible if backscatter X-ray images are available at a specific view angle.

FIG. 11 illustrates structural displacement after pressurization that might be visible if backscatter X-ray images are available at a specific view angle. Simply, in a structure 1100 bonds are to be made everywhere trusses 1102, 1104, 1106, and 1108 are adjacent to a skin 1110. While denoted by the upper illustration, but not visible, non-bonded region 1120 includes an area where upper members 1134 and 1136, respectively, of trusses 1104 and 1106 are not bonded to skin 1110. Application of pressure to structure 1100 causes a separation area 1150 to occur as shown in the lower illustration, in which the non-bond area 1120 is clearly seen as is the separation between skin 1100 and upper truss members 1134 and 1136.

The described embodiments are adaptable to other image acquisition technologies. For example, further embodiments utilize a traditional X-ray process whereby a digital detector is used to capture both a baseline image and a secondary image after the FOD has been moved within the structure or an internal component has been stressed that moves the underlying structure. As such, alternate X-ray technologies other than backscatter X-ray are also used to generate difference images of the internal structure.

The embodiments described herein are useful to all complex machine manufacturers and repair organizations, including, but not limited to, major aerospace manufacturers, water vehicle manufacturers, land vehicle manufacturers, and maintenance facilities. As described above, variations to movement of the structure to displace FOD embodiments include embodiments directed to non-destructive evaluation of structures. Examples of such non-destructive evaluation include, for example, a pressure or vacuum applied to a structure prior to acquisition of a second image to determine if a disbonding or other structural anomaly has occurred. More generally, a pre-stressed condition backscatter X-ray and a post-stressed condition backscatter X-ray may be utilized to determine if a movement has occurred with regard to the structure, for example, visualizing changes that occur internal to the structure and/or visualizing surface deformations caused by subsurface anomalies The embodiments described herein significantly increase the capability for detecting FOD and therefore reduce production costs associated with FOD as minimizing the amount of FOD left within products improves safety, customer relationships and improves the work process.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for detecting an anomaly associated with a structure, said method comprising:
   obtaining a baseline scan of the structure;
   changing at least one condition associated with the structure, the at least one condition intended to impart a movement of the structure or a movement of objects within the structure, wherein the at least one condition is changed by at least one of:
   applying at least one of a pressure, a vacuum, and a physical load to the structure; and
   moving the structure;
   obtaining a secondary scan of the structure, the secondary scan obtained from a same position, with respect to the structure, as the baseline scan;
   determining any differences between the baseline scan and the secondary scan; and
   identifying at least one of a foreign object proximate the structure and a structural anomaly associated with the structure based on any differences between the baseline scan and the secondary scan.

2. The method according to claim 1 wherein the at least one of the pressure, the vacuum, and the physical load is applied to the structure such that any disbonding or structural anomaly that results from the application also results in an imparted movement of the structure.

3. The method according to claim 1 wherein determining any differences between the baseline scan and the secondary scan comprises at least one of determining if any changes have occurred internal to the structure and determining if any surface deformations have occurred on the structure due to subsurface anomalies.

4. The method according to claim 1 wherein the structure is moved such that at least a portion of any foreign object debris associated with the structure changes position with respect to the structure.

5. The method according to claim 1 wherein moving the structure comprises at least one of:
   rotating the structure in an attempt to move any FOD therein;
   utilizing at least one of compressed air and pneumatics to attempt to move any FOD within the structure; and
   vibrating the structure to attempt to reposition any FOD therein.

6. The method according to claim 1 wherein:
   obtaining a baseline scan comprises obtaining a baseline backscatter X-ray scan; and
   obtaining a secondary scan comprises obtaining a secondary backscatter X-ray scan.

7. The method according to claim 1 wherein:
   obtaining a baseline scan comprises obtaining a baseline X-ray scan; and
   obtaining a secondary scan comprises obtaining a secondary X-ray scan.

8. The method according to claim 1 wherein determining any differences between the baseline scan and the secondary scan comprises comparing images associated with the respective scans and determining if an object moved from a first location in a first image to a second location in a second image.

9. The method according to claim 1 wherein obtaining a secondary scan of the structure, the secondary scan obtained from the same position comprises deploying a plurality of fiduciary position markers on the structure for alignment of a scanning device.

10. A method for determining whether any foreign object debris is associated with a structure, said method comprising:
    obtaining a baseline scan of the structure;
    causing a movement of the structure significant enough to cause a movement of any foreign object debris that is associated with the structure, wherein the movement is caused by at least one of:

moving the structure and returning it to its original position;

applying at least one of compressed air and pneumatic pressure to or within the structure; and vibrating the structure;

obtaining a secondary scan of the structure, the secondary scan obtained from a same position, with respect to the structure, as the baseline scan;

determining any differences between the baseline scan and the secondary scan; and identifying any foreign object debris associated with the structure based on the determined differences.

11. The method according to claim 10 wherein:

obtaining a baseline scan comprises obtaining a baseline backscatter X-ray scan; and obtaining a secondary scan comprises obtaining a secondary backscatter X-ray scan.

12. The method according to claim 10 wherein:

obtaining a baseline scan comprises obtaining a baseline X-ray scan; and obtaining a secondary scan comprises obtaining a secondary X-ray scan.

13. The method according to claim 10 wherein moving the structure comprises rotating the structure, the at least one of compressed air and pneumatic pressure is applied to move any foreign object debris associated with the structure, and the structure is vibrated to reposition any foreign object debris associated with the structure.

14. The method according to claim 10 wherein determining any differences between the baseline scan and the secondary scan comprises generating a difference image by subtracting any structure present in the same position in both the baseline scan and the secondary scan.

15. The method according to claim 10 wherein determining any differences between the baseline scan and the secondary scan comprises comparing images associated with respective scans and determining if an object moved from a first location in a first image to a second location in a second image.

16. The method according to claim 10 further comprising deploying a plurality of fiduciary position markers on the structure to ensure a scanning device is in the same position for both the baseline scan and the secondary scan.

17. The method according to claim 10 wherein the structure includes at least a portion of an aircraft.

18. A method for detecting foreign object debris and structural anomalies associated with an aircraft, said method comprising:

interrogating a portion of the aircraft with an X-ray source;

applying a physical load to the aircraft, wherein the physical load is applied by at least one of:

applying at least one of a pressure and a vacuum to the aircraft or within the portion of the aircraft; and moving the aircraft;

subsequently interrogating substantially the same portion of the aircraft with the X-ray source after the application of the physical load;

comparing images resulting from the X-ray interrogations to determine any differences; and identifying the objects or displacements that resulted in the differences as one of potential foreign object debris and a structural anomaly.

19. The method according to claim 18 wherein the at least one of the pressure and the vacuum is applied to the aircraft such that any disbonding or structural anomaly that results from the application also results in an imparted movement of the aircraft.

20. The method according to claim 18 wherein the aircraft is moved such that at least a portion of any foreign object debris associated with or within the same portion of the aircraft changes position with respect to the aircraft.

* * * * *